United States Patent
Zhang

(10) Patent No.: US 10,736,833 B1
(45) Date of Patent: Aug. 11, 2020

(54) OIL-FREE HAIR AND SCALP CONDITIONING ADDITIVE

(71) Applicant: Baolong Zhang, Hangzhou (CN)

(72) Inventor: Baolong Zhang, Hangzhou (CN)

( * ) Notice: Subject to any disclaimer, the term of this patent is extended or adjusted under 35 U.S.C. 154(b) by 0 days.

(21) Appl. No.: 16/830,200

(22) Filed: Mar. 25, 2020

(51) Int. Cl.
| | |
|---|---|
| *A61K 8/67* | (2006.01) |
| *A61K 8/37* | (2006.01) |
| *A61K 8/64* | (2006.01) |
| *A61K 8/49* | (2006.01) |
| *A61Q 5/12* | (2006.01) |

(52) U.S. Cl.
CPC ............... *A61K 8/678* (2013.01); *A61K 8/37* (2013.01); *A61K 8/4946* (2013.01); *A61K 8/4973* (2013.01); *A61K 8/645* (2013.01); *A61Q 5/12* (2013.01)

(58) Field of Classification Search
CPC .......... A61K 8/678; A61K 8/37; A61K 8/645; A61K 8/4973; A61K 8/4946; A61Q 8/12
See application file for complete search history.

(56) References Cited

U.S. PATENT DOCUMENTS

2017/0087199 A1\* 3/2017 Patron ................... A61K 36/81

\* cited by examiner

*Primary Examiner* — Nannette Holloman

(57) ABSTRACT

The invention discloses an oil-free additive for hair and scalp conditioning, which includes the following ingredients in percentage: 50% pure water, 5% sodium stearoyl lactylate, 10% vitamin E, 10% histidine, 1.5% anhydroxylitol, 3.5% hydrolyzed wheat protein, 7% allantoin, 5% hydrolyzed albumen and 8% carnosine. The invention has following characteristics:

1. It is the first oil-free formula in the field of hair care, so related products produced with the additive will not block hair follicles on scalps, thus leaving no residue and bringing no burden to hair care;
2. It can effectively reduce chemical damages occurred during hair perming and dyeing, and neutralize chemical residue;
3. Being non-irritating and corrosion preventing, it neutralizes residual calcium compounds in the hair, calcium carbonate and magnesium carbonate, thereby inhibiting hair splitting effectively;
4. It can greatly reduce adverse effects of organic compounds on human skin and hair, and play a role of preventing alopecia and oxidation, moisturizing and protecting skin from sun exposure. In addition, it is completely biodegradable and environment-friendly.

3 Claims, No Drawings

OIL-FREE HAIR AND SCALP CONDITIONING ADDITIVE

TECHNICAL FIELD

The invention relates to a hair care product, and more particularly to an oil-free additive for hair and scalp conditioning.

BACKGROUND TECHNOLOGY

Currently, most consumers know about silicone oil-free shampoos and keep on using them, but pay little attention to the silicone oil (polydimethylsiloxane) contained in the hair care products used. Actually, most of hair care products in the prior art contain silicone oil (polydimethylsiloxane), which damages hair and scalp in long-term using. It is easy to cover surface of hair and scalp, but difficult to clean, which causes excessive oil dandruff wrapping hair to block absorption of nutrients, thereby hair oxidative deterioration, hardening and yellowing easily. Damages caused by perming and dyeing are beyond repair and will even result in hair loss due to blocked follicles. Consequently, the results deviate from the original purpose and effects of using a silicone-free shampoo.

On the other hand, some consumers, especially women, have long been plagued by hair-end splitting. Shampoo can clean dirt on the surface of the hair, but it is difficult to remove calcium compounds (calcium carbonate and magnesium carbonate) in the hair formed by residues such as calcium and magnesium from water. Oil wrapping accelerates hair splitting.

Therefore, it is an imperative problem for technicians in the art to research an oil-free additive for hair and scalp conditioning to solve above problems and neutralize chemicals impurities from perming and dyeing as well as water impurities remaining in the hair.

Content of the Invention

In view of this, the invention provides an oil-free additive for hair and scalp conditioning, anti-oxidative and oil-free and, can moisturize, nourish and soften hair, bring no burden on scalp by neutralizing residual impurities and prevent splitting.

To achieve the above objectives, the invention provides the following technical solutions:

An oil-free additive for hair and scalp conditioning is characterized by a composition including pure water, sodium stearoyl lactylate, vitamin E, histidine, anhydroxylitol, hydrolyzed wheat protein, allantoin, hydrolysis albumen and carnosine.

Preferably, the above-mentioned oil-free additive for hair and scalp conditioning includes following ingredients in percentage: 50% pure water, 5% sodium stearoyl lactylate, 10% vitamin E, 10% Histidine, 1.5% anhydroxylitol, 3.5% hydrolyzed wheat protein, 7% allantoin, 5% hydrolyzed albumen, and 8% carnosine.

Preferably, in the above-mentioned oil-free hair and scalp conditioning additive, 5% sodium stearoyl lactylate and 65-degree pure water are used for emulsification.

Effects of the ingredients of the invention are as follows:

Vitamin E, a fat-soluble vitamin, is an important component and a major antioxidant of cell membranes. It protect scalp from oxidation, ultraviolet rays and pollution, and prevent scalp cells from the toxic free radicals, thereby effectively reducing scalp wrinkles, scalp inflammation and hair loss, and decreasing pigmentation.

Histidine is an active protein center, whose main functions are to promote absorption of nutrients, resist static electricity and sunlight.

Anhydroxylitol is used as a humectant to strengthen the absorption of nutrients.

Hydrolyzed wheat protein mainly contains amino acids such as gliadin and gluten protein, which are rich in cystine, playing a role of moisturizing and anti-oxidation, and in refining, nourishing and softening hair.

Allantoin protects hair from splitting and breaking, and takes effects of avoiding light, sterilization, antisepsis and anti-oxidation to nourish and soften hair.

Hydrolyzed albumen is a functional protein that can be absorbed by scalp and hair, and a nutrient to improve the efficacy of active substances. With surface activity, albumen also acts as an emulsifier and a foam stabilizer.

Carnosine is a small-molecule peptide that has significant effects on anti-aging, anti-oxidation, and can inhibit free radicals and lipid oxidation caused by metal ions, thereby enhancing the anti-oxidation ability of scalp and hair.

The above technical solutions indicate that compared with the prior art, the invention has the following characteristics:

Composed of pure water, sodium stearoyl lactylate, vitamin E, histidine, anhydroxylitol, hydrolyzed wheat protein, allantoin, hydrolyzed albumen and carnosine, it is a truly oil-free hair care product, which will not wrap hair follicles and hair, bring burden to scalp and hair, or leave residues. Therefore, hair care products with this additive will not wrap scalp and hair follicles, and bring burden to the hair.

The invention can effectively reduce chemical damages to hair during perming and dyeing, and neutralize relevant chemical residues.

The invention has a non-irritating and antiseptic effect, while neutralizing residual calcium compounds like calcium carbonate and magnesium carbonate in the hair, thereby preventing hair splitting effectively.

The invention can greatly reduce adverse effects of organic compounds on human skin and hair, and play a role of preventing alopecia and oxidation, moisturizinge and protecting skin from sun exposure. In addition, it is completely biodegradable and environment-friendly.

EMBODIMENTS

Technical solutions in embodiments of the invention are described clearly and completely in combination with the embodiments. It is obvious that the described embodiments are only a part of the embodiments of the present invention, but not all. Based on the embodiments of the invention, all others embodiments obtained by general technicians in the art without creative efforts shall be protected with the invention.

The invention discloses an oil-free additive for hair and scalp conditioning, which is anti-oxidative and oil-free, and can moisturize, nourish and soften hair and protect hair from splitting by neutralizing the residual impurities while no burden is imposed on the scalp.

Please refer to an oil-free additive for hair and scalp conditioning disclosed in the invention, which specifically includes: pure water, sodium stearoyl lactylate, vitamin E, histidine, anhydroxylitol, hydrolyzed wheat protein, allantoin, hydrolyzed albumen and carnosine.

In order to optimize the above technical solution, following ingredients in percentage are included: 50% pure water, 5% sodium stearoyl lactylate, 10% vitamin E, 10% histidine, 1.5% anhydroxylitol, 3.5% hydrolyzed wheat protein, 7% allantoin, 5% hydrolyzed albumen and 8% carnosine.

In order to optimize the above technical solution, 5% sodium stearoyl lactylate is mixed with 65-degree pure water for emulsification.

Cases of Users:

Lin, female, is a 22-year-old college student, whose hair was damaged seriously and broken easily after several times bleaching and dyeing. She had used many hair care products, but hair was still fragile and lack of toughness. After using this product for 8 times, her hair recovered toughness that it won't be fragile and break in water.

Chen, a 32-year-old man, who has alopecia and oily hair. Improvements were found in oily hair after he used this product 3 times, once every 2 days, and alopecia was controlled after 5 times.

Zhang, a 40-year-old woman, whose hair was splitting and difficult to comb. She used the product once every 2 days. After one month, the hair became non-splitting, shiny and non-shedding.

Wang, a 33-year-old woman, whose hair became dry with a smell of chemicals because of perming. She used the product once every 2 days. After 3 times, the smell of chemicals for perming disappeared and the hair became moist and shiny.

The embodiments in this description are described in a progressive manner. Key points of each are different from others. The same and similar parts of various embodiments can be referred with each other. Devices disclosed in the embodiments are simply described as they correspond to the method disclosed therein. Relevant details can refer to the description of the method.

The above description of the disclosed embodiments enables technicians in the art to implement or use the invention. Various modifications to these embodiments are explicit to technicians in the art. The general principles defined herein can be implemented in other embodiments without departing from the spirit or scope of the invention. Therefore, the invention will not be limited to the embodiments shown herein, but should conform to the widest scope consistent with the principles and novel features disclosed herein.

The invention claimed is:

1. An oil-free hair and scalp conditioning additive characteristically contains pure water, sodium stearoyl lactylate, vitamin E, histidine, anhydroxylitol, hydrolyzed wheat protein, allantoin, hydrolyzed albumen and carnosine.

2. An oil-free hair and scalp conditioning additive according to claim 1 characteristically contains following ingredients in percentage: 50% pure water, 5% sodium stearoyl lactylate, 10% vitamin E, 10% histidine, 1.5% anhydroxylitol, 3.5% hydrolyzed wheat protein, 7% allantoin, 5% hydrolyzed albumen and 8% carnosine.

3. An oil-free hair and scalp conditioning additive according to claim 1 is characterized by emulsification of 5% sodium stearoyl lactylate and 65-degree pure water.

* * * * *